United States Patent [19]

Kachhy et al.

[11] Patent Number: 4,689,425
[45] Date of Patent: Aug. 25, 1987

[54] PHOTOCHLORINATION OF AROMATIC COMPOUNDS IN THE SIDE CHAIN

[75] Inventors: Avinash Kachhy, Edison; Henry J. Barda, North Brunswick, both of N.J.

[73] Assignee: Stauffer Chemical Company, Westport, Conn.

[21] Appl. No.: 927,477

[22] Filed: Nov. 6, 1986

[51] Int. Cl.$^4$ ............................................. C07C 69/76
[52] U.S. Cl. ................................... 560/103; 562/493; 204/157.89
[58] Field of Search ................ 560/103; 562/493; 204/157.89

[56] References Cited

U.S. PATENT DOCUMENTS

| | | | |
|---|---|---|---|
| 3,109,799 | 11/1963 | Katzschmann | 204/157.89 |
| 3,113,084 | 12/1963 | Blardenelli | 204/157.89 |
| 3,152,055 | 10/1964 | Katzschmann | 204/117.89 |
| 3,230,268 | 1/1966 | Kobayashi et al. | 560/103 |
| 3,704,215 | 11/1972 | Bockmann | 204/157.89 |
| 4,172,098 | 10/1979 | Scheuermann et al. | 560/103 |

FOREIGN PATENT DOCUMENTS

| | | | |
|---|---|---|---|
| 228944 | 5/1958 | Australia | 560/103 |
| 2005727 | 1/1977 | Japan | 562/493 |
| 7470946 | 7/1984 | Japan | 562/493 |
| 773131 | 4/1957 | United Kingdom | 562/493 |
| 884114 | 12/1961 | United Kingdom | 562/493 |

OTHER PUBLICATIONS

CA 58, 4574h, Helv. Chim. Acta 45 (1860–1870), 1962.

*Primary Examiner*—Paul J. Killos
*Attorney, Agent, or Firm*—Hensley M. Flash

[57] ABSTRACT

A process for photochlorinating aromatic compounds in the side chain and, in particular, a process for the selective chlorination of a 2-alkyl group of 2-alkyl benzoic acid or ester is disclosed. In this process, hydrogen chloride is added to the benzoic acid or ester prior to adding chlorine in the presence of actinic radiation at a reaction temperature below the decomposition temperature of the resulting chlorinated acid or ester. A typical aromatic compound is methyl 2-methylbenzoate and the reaction is preferably carried out at a temperature ranging from about −20° C. to 20° C.

9 Claims, No Drawings

PHOTOCHLORINATION OF AROMATIC COMPOUNDS IN THE SIDE CHAIN

BACKGROUND OF THE INVENTION

1. Field of the Invention

This invention relates to a process for selectively chlorinating aromatic compounds in the side chain and, particularly, to a process for chlorinating the 2-alkyl group of 2-alkyl benzoic acid or ester.

2. Related Information

Halogen-containing aromatic compounds are well-known, versatile intermediates. In particular, 2-alkyl benzoic acid or esters which have been chlorinated at the 2-alkyl group, e.g., methyl 2-(chloromethyl)benzoate (MCMB), otherwise known as alpha-chloro-o-toluic acid methyl ester, is a well-known intermediate for a rice herbicide.

The known processes for preparing esters of, for example, chloromethylbenzoic acid, are comparatively complicated and difficult to practice. British Patent Specification No. 773,131, dated Apr. 24, 1957, discloses the preparation of esters of chloromethylbenzene carboxylic acids by the chlorination with gaseous chlorine at a temperature of between 80° C. and 170° C. of esters of p-toluic acid. Japan Kokai No. 7470.946, dated July 9, 1974, as abstracted in Chem. Abstracts 81.135759x, discloses the preparation of methyl p-(monochloromethyl)benzoate by the chlorination of methyl para-toluate with chlorine under UV radiation at 20° C. to 70° C.

Attempts to photochlorinate 2-alkylbenzoic ester, e.g., methyl 2-methylbenzoate (MMB), resulted in difficulties because of thermal instability at relatively low temperatures, for example, 60° C. for MCMB which degraded to a phthalide degradation product. Consequently, attempts to obtain product relatively free of phthalide impurities were frustrated.

SUMMARY OF THE INVENTION

An object of this invention is to provide a method for selectively chlorinating the 2-alkyl group of 2-alkyl benzoic acid or ester to yield the chlorinated acid or ester in good yield. A further object is to achieve this chlorination at low reaction temperatures, thereby minimizing the degradation of the chlorinated product into phthalide by-products.

Other objects and advantages of the present invention are described elsewhere within this specification.

This invention is a process for the selective chlorination of a 2-alkyl group of 2-alkyl benzoic acid or ester which comprises adding hydrogen chloride to the benzoic acid or ester prior to adding chlorine in the presence of actinic radiation at a reaction temperature below the decomposition temperature of the resulting chlorinated acid or ester. In this process, the 2-alkyl group can contain from 1 to 20 carbon atoms, and the process is usually carried out below room temperature and preferably at a temperature ranging from about −20° C. to 20° C.

DETAILED DESCRIPTION OF THE INVENTION

Side chain chlorinations of aromatic compounds are usually carried out above 80° C. This is because lower temperatures are conducive to nuclear chlorination and it is more difficult to sustain free radical chain reactions at lower temperatures. However, when the resulting chlorinated products are thermally unstable, a problem results. Chlorinated 2-alkyl benzoic acid or esters are particularly susceptible to forming phthalide degradation products at elevated temperatures.

When attempts were made to chlorinate 2-alkyl benzoic acid or esters, e.g., methyl 2-methylbenzoate (MMB) at lower temperatures, the reaction could not be initiated. For example, when chlorine was introduced at 6 g/hr. in the presence of UV light into a mole of MMB, kept at −2° C., no reaction was observed as evidenced by exotherm, loss of chlorine color, or hydrogen chloride evolution. However, it was discovered that if the 2-alkyl benzoic acid or ester, e.g., MMB, was first saturated with hydrogen chloride, the reaction was initiated after a few minutes of chlorine sparging. This reaction initiation was indicated by a rise in temperature and the accompanying disappearance of the accumulated chlorine color.

The aromatic compound in which the alkyl side chain is photochlorinated can include a 2-alkyl benzoic moiety. This moiety can be an acid or the hydrogen in the acid can be replaced with an alkyl group or a hydrocarbyl group. The alkyl side chain in the 2-position can contain from 1 to 20 carbon atoms, and the the chain of carbon atoms can be branched or straight. Preferred aromatic compounds include 2-alkyl benzoic acid or ester, and a particularly preferred compound is methyl 2-methyl benzoate.

The process is generally carried out by introducing a stream of gaseous hydrogen chloride into the 2-alkyl benzoic acid or ester. The flow rate of the hydrogen chloride should preferably not exceed is rate of absorption, and the use of amounts of hydrogen chloride above its saturation point is not preferred. Chlorine gas is then introduced into the reaction mixture. The flow rate of the chlorine gas can be selected to minimize chlorine loss, i.e., chlorine not dissolved, and to minimize color build-up in the reactants which can interfere with the initiating light radiation. A maximum flow rate of about 6 g/hr. is recommended at 1° C.

The chlorine gas is introduced into the reaction mixture in the presence of actinic radiation. This actinic radiation can include radiant energy ranging from the visible spectral regions through the extreme ultraviolet spectral regions, and preferably ranging from about 590 nanometers to about 50 nanometers, with a range from about 425 nanometers to about 370 nanometers being particularly preferred.

During the above processing steps, the reaction temperature can be maintained from about −20° C. to about 60° C., and preferably below room temperature with a temperature range from about −20° C. to 20° C. being particularly preferred. The upper end of the reaction temperature range can be limited to the decomposition temperature of the resulting chlorinated acid or ester. At the lower end of this temperature range, it can be advantageous to include a free radical initiator, for example, di-tertiary butyl peroxide, and azobisisobutyronitrile.

This process is a selective chlorination in which the monochloro ester content is optimized by employing about 50% to 120% of the theoretical amount of chlorine necessary for monochlorination.

The following experiments describe various embodiments of the invention. Other embodiments will be apparent to one of ordinary skill in the art from a consideration of the specification or practice of the invention disclosed therein. It is intended that the specification and experiments be considered as exemplary only with the true scope and spirit of the invention being indicated by the Claims which follow the experiments.

EXPERIMENTS

The apparatus used in the experiments described below included a 250 ml three-neck flask provided with a thermometer, magnetic stirrer, sparger, and air condenser. The condenser was connected to a scrubber. The light source was a Black Ray ®, Long Wave UV Lamp, Model B-100A, supplied by Ultraviolet Products, Inc., San Gabriel, Calif., placed one foot away from the flask and directed at a 45° angle from above. The flask was placed in a plastic bath through which circulated a water/diethyleneglycol mixture from a Fisher Scientific Model 9000 Refrigerated Constant Temperature Bath and Circulator. The gases were introduced through a calibrated Gilmont No. 11 Flowmeter. The following paragraph summarizes several experiments that were performed.

Methyl 2-methyl benzoate (MMB, 150.2 g, 1 mole) was added to the flask and cooled to −5° C. The UV light was turned on and hydrogen chloride sparged at 20 g/hr. for one hour (200 standard mls. of air/minute flowmeter reading). The temperature rose to 0° C. and started to drop when saturation was reached. Chlorine was then added at 6 g/hr. for 15 minutes (30 standard mls. of air/minute flowmeter reading). Whereupon, the yellow chlorine color which had accumulated disappeared, indicating the reaction had initiated. At this point, the chlorine flow rate was either increased to 11.4 g/hr. (60 standard mls. of air/minute flowmeter reading) which is the maximum amount of chlorine capable of being taken up under these reaction conditions, or continued at 6 g/hr. At 6 g/hr. chlorine addition, the temperature stabilized at $-3\pm1°$ C., while at 11.4 g/hr. the temperature stabilized at $1\pm1°$ C. A total of $79\pm5$ g ($1.11\pm0.07$ moles) of chlorine was added for an addition time of 13.2 hours at 6 g/hr. or 7.1 hours at 11.4 g/hr. The weight of chlorine added was confirmed by weighing the chlorine cylinder. The UV light was left on for half an hour after the chlorine addition was terminated. The temperature of the reactants was increased to range from 21° C. to 25° C. and the pressure was gradually decreased to 21 inches of vacuum. These conditions were held for one hour. This brought the hydrogen chloride content down to 0.4 weight percent. Nitrogen was then sparged at an estimated rate of 7.9 g/hr. for one hour (200 standard mls. of air/minute flowmeter reading) to bring the hydrogen chloride level to 0.1 weight percent.

The resulting product weighed $187.1\pm2.3$ g, for an average chlorine consumption efficiency of 96% and analyzed as $74\pm1$ area percent of methyl 2-(chloromethyl)benzoate (MCMB $75.0\pm0.9\%$ yield) and $10.5\pm1.5$ area percent of unreacted MMB.

It was noted that if the reaction was interrupted and had to be resumed, the hydrogen chloride addition step had to be repeated to initiate the reaction.

What is claimed is:

1. A process for the selective chlorination of a 2-alkyl group of 2-alkyl benzoic acid or ester which comprises adding hydrogen chloride to the benzoic acid or ester prior to adding chlorine in the presence of actinic radiation at a reaction temperature below the decomposition temperature of the resulting chlorinated acid or ester.

2. The process of claim 1 wherein the 2-alkyl group has from 1 to 20 carbons.

3. The process of claim 1 wherein the reaction is carried out at a temperature ranging from about 31°° C. to about 60° C.

4. The process of claim 1 wherein the reaction is carried out below room temperature.

5. The process of claim 1 wherein the reaction is carried out at a temperature ranging from about −20° C. to 20° C.

6. The process of claim 5 wherein the reaction is carried out in the presence of a free radical initiator.

7. The process of claim 1 wherein the ester is methyl 2-methylbenzoate.

8. The process of claim 7 wherein the reaction is carried out at a temperature ranging from about −20° C. to 20° C.

9. The process of claim 8 wherein the reaction is carried out in the presence of a free radical initiator.

* * * * *

UNITED STATES PATENT AND TRADEMARK OFFICE
CERTIFICATE OF CORRECTION

PATENT NO. : 4,689,425
DATED : August 25, 1987
INVENTOR(S) : A. Kachhy et al.

It is certified that error appears in the above—identified patent and that said Letters Patent is hereby corrected as shown below:

Col. 2, line 33, "is" should read -- its --; and

Col. 4, line 28, "31°C" should read -- -20°C --.

Signed and Sealed this

Twenty-ninth Day of March, 1988

Attest:

DONALD J. QUIGG

Attesting Officer    Commissioner of Patents and Trademarks